US008236095B1

(12) United States Patent
Bassine

(10) Patent No.: US 8,236,095 B1
(45) Date of Patent: Aug. 7, 2012

(54) VACUUM-PRESSURE SWING ABSORPTION CONCENTRATOR

(75) Inventor: Stuart Bassine, Hendersonville, NC (US)

(73) Assignee: O2 Concepts, LLC, Oklahoma City, OK (US)

( * ) Notice: Subject to any disclaimer, the term of this patent is extended or adjusted under 35 U.S.C. 154(b) by 474 days.

(21) Appl. No.: 12/589,159

(22) Filed: Oct. 19, 2009

Related U.S. Application Data

(60) Provisional application No. 61/196,441, filed on Oct. 17, 2008.

(51) Int. Cl.
  *B01D 53/02* (2006.01)
(52) U.S. Cl. ............ 96/114; 96/113; 96/133; 96/143; 95/95; 95/102; 95/104; 95/130; 95/148; 128/200.24; 128/204.18; 128/204.21; 128/204.22; 128/205.11
(58) Field of Classification Search ............. 95/95–98, 95/102, 104, 105, 130, 148; 96/113, 114, 96/133, 143; 128/200.24, 204.18, 204.21, 128/204.22, 205.11
See application file for complete search history.

(56) References Cited

U.S. PATENT DOCUMENTS

| | | | | | |
|---|---|---|---|---|---|
| 4,065,272 | A | * | 12/1977 | Armond | 95/101 |
| 4,869,733 | A | * | 9/1989 | Stanford | 95/19 |
| 5,968,236 | A | * | 10/1999 | Bassine | 96/130 |
| 6,056,804 | A | * | 5/2000 | Keefer et al. | 95/96 |
| 6,143,056 | A | * | 11/2000 | Smolarek et al. | 95/96 |
| 6,478,850 | B1 | * | 11/2002 | Warren | 95/21 |
| 7,455,717 | B2 | * | 11/2008 | Sprinkle | 95/22 |
| 7,491,040 | B2 | * | 2/2009 | McCombs et al. | 417/545 |
| 7,510,601 | B2 | * | 3/2009 | Whitley et al. | 96/121 |
| 7,771,511 | B2 | * | 8/2010 | Dolensky | 95/96 |
| 8,016,925 | B2 | * | 9/2011 | McCombs et al. | 96/121 |
| 8,020,553 | B2 | * | 9/2011 | Jagger et al. | 128/201.25 |
| 8,070,853 | B2 | * | 12/2011 | Sprinkle | 95/22 |
| 8,142,544 | B2 | * | 3/2012 | Taylor et al. | 95/22 |
| 2002/0127442 | A1 | * | 9/2002 | Connor et al. | 429/12 |
| 2005/0047947 | A1 | * | 3/2005 | McCombs et al. | 417/545 |
| 2005/0072426 | A1 | * | 4/2005 | Deane et al. | 128/204.26 |
| 2006/0137522 | A1 | * | 6/2006 | Nishimura et al. | 95/96 |
| 2006/0266357 | A1 | * | 11/2006 | McCombs et al. | 128/204.26 |
| 2007/0227360 | A1 | * | 10/2007 | Atlas et al. | 96/121 |
| 2008/0105258 | A1 | * | 5/2008 | Deane et al. | 128/204.21 |
| 2008/0110338 | A1 | * | 5/2008 | Taylor et al. | 95/21 |
| 2009/0211448 | A1 | * | 8/2009 | McClain | 95/211 |

* cited by examiner

*Primary Examiner* — Robert J Hill, Jr.
*Assistant Examiner* — Christopher P Jones
(74) *Attorney, Agent, or Firm* — Crowe & Dunleny

(57) ABSTRACT

A vacuum-pressure swing absorption concentrator includes a motor driven compressor having pressure and vacuum heads that are connected to a pressure reservoir and a vacuum reservoir respectively. The pressure and vacuum reservoirs are selectively and alternately interconnected in sequence through a main valve to a pair of nitrogen filtering sieve beds. A controller operates the valve to alternately and cyclically interconnect the sieve beds to the pressure and vacuum reservoirs respectively. During each cycle, a respective bed is pressurized and enriched oxygen is produced and delivered to a tank for use by a patient. At the same time, the other bed is evacuated through the vacuum reservoir. A crossover valve delivers oxygen from a pressurized bed to an evacuated bed to facilitate purging of impurities previously collected in the evacuated bed.

13 Claims, 2 Drawing Sheets

VACUUM-PRESSURE SWING ABSORPTION CONCENTRATOR

RELATED APPLICATION

Figure 1:
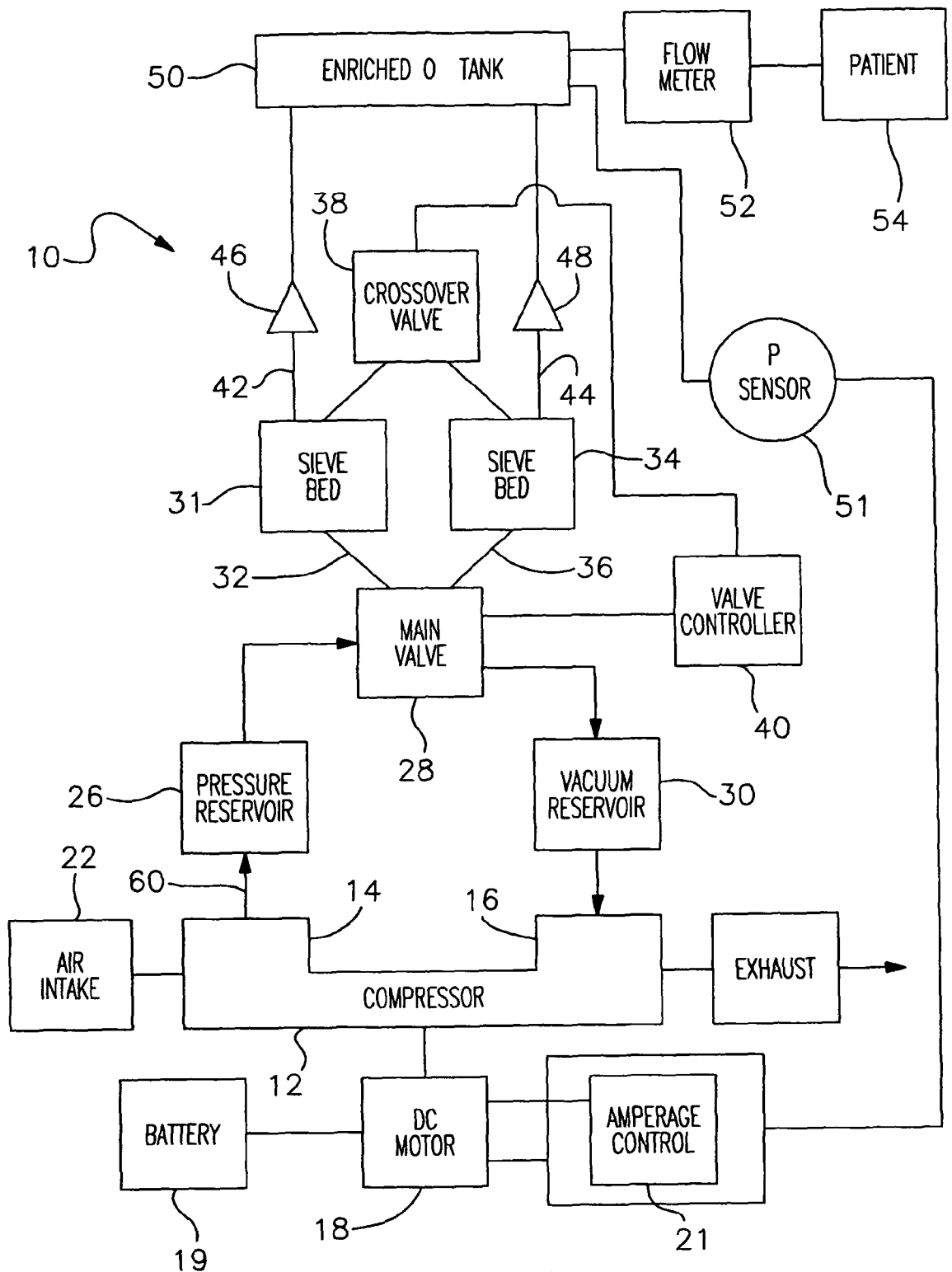

This application claims the benefit of U.S. Provisional Patent Application Ser. No. 61/196,441 filed Oct. 17, 2008.

FIELD OF THE INVENTION

This invention relates to an oxygen concentrator that produces enriched oxygen for medical purposes utilizing vacuum-pressure swing absorption. More particularly, the concentrator exhibits a highly efficient operation by incorporating pressure and vacuum reservoirs between the compressor and sieve beds.

BACKGROUND OF THE INVENTION

Oxygen concentrators are commonly used to provide enriched oxygen to patients having respiratory problems. Conventional concentrators typically operate on the principles of pressure swing absorption, vacuum swing absorption or vacuum-pressure swing absorption. According to these techniques, air is delivered under pressure to a sieve bed wherein nitrogen and other impurities are absorbed by a filter medium such as zeolite. The trapped air impurities are then purged and vented under reduced pressure or vacuum conditions. In some devices, pressurized air is delivered sequentially to two or more beds in an attempt to improve the efficiency of the system.

Despite advancements in medical concentrator technology, known products are still far from optimally efficient. The compressor used in most such products must generate pressure and air flow that are sufficient to produce an adequate volume of enriched oxygen for the patient. This typically requires the compressor and associated motor to draw a substantial amount of electrical power. Portable concentrators utilize consumable batteries and the significant power demands of such concentrators tend to shorten battery life considerably. In addition, the body of a typical portable concentrator is apt to heat up excessively when operating under the high pressure generated by the compressor. This further reduces the operating efficiency of the apparatus. Moreover, if a compressor operating under high pressure delivers a volume of air to the sieve beds faster than those beds can process the air, the motor driving the concentrator's compressor is apt to stall.

A further disadvantage exhibited by standard concentrators is that the motor is usually controlled to operate at a constant speed (RPM). This tends to produce an inadequate volume of air over the concentrator cycle. If the operating speed is increased to increase air flow, excessive power is consumed and battery life is shortened.

SUMMARY OF THE INVENTION

It is therefore an object of the present invention to provide an extremely efficient vacuum-pressure swing absorption concentrator that produces and delivers to the patient large and effective volumes of enriched oxygen while requiring significantly less power than covered by conventional medical concentrators.

It is a further object of this invention to provide a medical concentrator that requires significantly less power to produce desired volumes of enriched oxygen so that battery life is significantly prolonged.

It is a further object of this invention to provide an efficient vacuum-pressure swing absorption oxygen concentrator that is particularly effective for portable use.

It is a further object of this invention to provide a vacuum-pressure swing absorption concentrator that produces much less heat than conventional medical concentrators.

It is a further object of this invention to provide a vacuum-pressure swing absorption concentrator that reduces the amount of moisture introduced into the sieve beds so that improved filter performance is achieved.

It is a further object of this invention to provide an oxygen concentrator that improves sieve bed efficiency and concentrator portability by reducing the amount of filter medium and the size of the sieve beds needed to produce a desired volume of enriched oxygen.

It is a further object of this invention to provide an oxygen concentrator that employs an amperage controlled motor in order to produce increased volumes of enriched oxygen while requiring less power than concentrators using a speed controlled motor.

It is a further object of this invention to provide an oxygen concentrator that employs main and crossover valves featuring equal air flow volumes during alternating flow cycles so that improved filtering efficiency and oxygen output are achieved.

It is a further object of this invention to provide an oxygen concentrator that introduces enriched oxygen from the filter head being pressurized to the other bed being evacuated before the end of each pressurization cycle so that improved nitrogen filtration is achieved and less power is required.

This invention results from a realization that the operating efficiency of a vacuum-pressure swing absorption concentrator is improved significantly by installing both pressure and vacuum reservoirs between the compressor and the sieve beds of the machine. This permits an effective high volume of air flow to be generated through the filter medium of the sieve beds. At the same time, reduced pressure and vacuum forces are exerted upon the compressor. As a result, the concentrator operates much more efficiently and effectively, and requires significantly less power than is used by conventional machines.

This invention features a vacuum-pressure swing absorption concentrator for delivering enriched oxygen to a medical patient. The concentrator includes a motor driven compressor having intake and exhaust ports. The air intake port is communicably connected to a pressure reservoir, which accommodates air pressurized by the compressor. The pressure reservoir includes an outlet that is communicably connected to a main valve. The main valve sequentially and alternately interconnects the pressure reservoir to communicate with a selected one of a pair of nitrogen filters or sieve beds while communicably interconnecting the other bed with a vacuum reservoir. The vacuum reservoir includes an outlet that is communicably interconnected to the exhaust port of the compressor. The main valve is operated to deliver air from the pressure reservoir to a selected one of the sieve beds for filtering while simultaneously discharging or evacuating previously filtered impurities from the other sieve bed. Enriched oxygen, which has been filtered by the sieve beds, is then directed to a tank for ultimate delivery to a patient using the concentrator.

In a preferred embodiment, the compressor includes a pair of heads for generating air under pressure and a vacuum respectively. A motor control mechanism preferably featuring amperage control directs the motor to operate at a relatively constant predetermined power. This achieves a greater air flow and more effective and efficient filtering than is obtained using concentrators wherein the speed (RPM) of the motor is controlled.

A controller may be utilized to operate the main valve so that the sieve beds are alternately and sequentially interconnected to the pressure and vacuum reservoirs. A crossover valve may be interconnected between the sieve beds. The controller, which may comprise a known type of microprocessor, typically also directs the crossover valve to open shortly before each sieve bed is fully pressurized. Oxygen is thereby delivered to the other sieve bed (i.e. the bed being evacuated) and this helps to purge filtered nitrogen and other impurities from that bed and further reduces system pressure. The crossover valve delivers a precise, equal volume of enriched oxygen alternately to each bed as that bed is under vacuum. This improves overall oxygen production. If unequal volumes are delivered (as in the prior art), one of the beds overworks and the efficiency and overall oxygen concentration generated by the concentrator are significantly reduced. Check valves may be provided between the sieve beds and the enriched oxygen tank to direct the flow of enriched oxygen in one direction from the beds to the tank while restricting oxygen flow in the opposite direction.

DETAILED DESCRIPTION OF PREFERRED EMBODIMENTS

Figure 2:
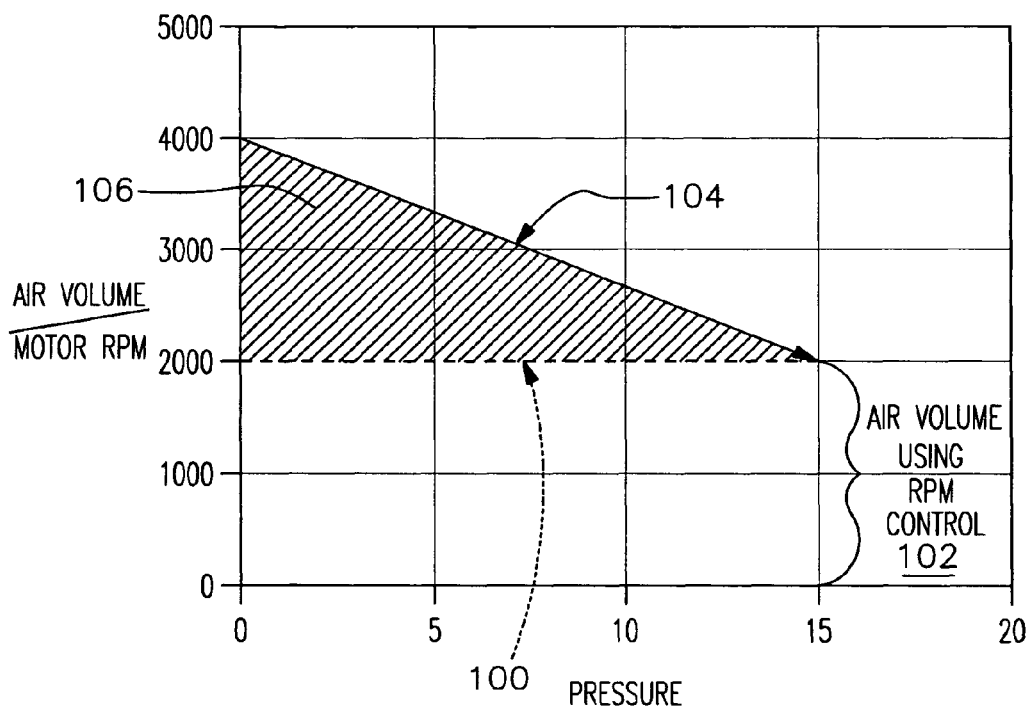

Other objects, features and advantages will occur from the following description of a preferred embodiment and the accompanying drawings, in which:

FIG. 1 is a schematic view of the vacuum-pressure swing absorption concentrator of this invention; and FIG. 2 is a graph that depicts the relative volumes of air produced by the compressor using amperage motor control as disclosed by this invention versus standard RPM motor control.

There is shown in FIG. 1 a vacuum-pressure swing oxygen concentrator 10 for delivering enriched oxygen to a medical patient. The components of concentrator 10 are particularly effective for use in portable, battery powered concentrators although the particular intended use of the concentrator is not a limitation of this invention.

Concentrator 10 includes a compressor 12 having a pressure generating section or head 14 and a vacuum generating section or head 16. The compressor is operated by a DC motor 18 featuring an amperage control circuit 20, which may comprise a portion or all of DC motor control 21. Motor 18 is, in turn, energized by a battery power supply 19. As compressor 12 is operated in accordance with this invention, fresh air is drawn into the compressor through an air intake 22 and filtered in a manner described more fully below. After the filtration is performed and enriched oxygen is generated, filtered impurities are discharged by an exhaust port 24. Conventional compressors and associated components that perform the foregoing functions will be known to persons skilled in the art.

A pressure reservoir 26 comprising an aluminum tank includes an inlet that is communicably connected to pressure head 14 of compressor 12. An outlet of pressure reservoir 26 is likewise communicably connected to an inlet of main control valve 28. The main valve also includes an outlet that is communicably connected to the inlet of a vacuum reservoir 30. The vacuum reservoir may again comprise a tank composed of aluminum or similar durable material. Vacuum head 16 of compressor 12 is communicably connected to an outlet of vacuum reservoir 30. The communicable connections disclosed herein may be attached by conventional means such as tubes, pipes, hoses or other forms of conduits.

Valve 28 is communicably joined to a first sieve bed 31 by a first sieve bed connection 32. The main valve is likewise communicably joined to second sieve bed 34 by a second sieve bed connection 36. The sieve beds (also referred to as nitrogen filters) typically include a standard filtering medium used in the medical oxygen concentrator industry. Various filter compositions (e.g. zeolite) may be employed within the scope of this invention. The size of each sieve bed may range from approximately the size of the pressure reservoir to a volume ten times greater than that of reservoir 26. Beds 30 and 34 are themselves interconnected by a crossover valve 38 that is selective opened, as described below, to communicably join the beds.

Main valve 28 is constructed so that sieve beds 31 and 34 may be selectively, sequentially and alternately interconnected with pressure reservoir 26 and vacuum reservoir 30 respectively. Such alternating and selective communicable interconnection is accomplished by constructing main valve 28 in accordance with a variety of valves available in the industry and known to persons skilled in the art. Typically, valve 28 exhibits a timed operation controlled by a controller 40, which typically comprises a microprocessor that is programmed to perform timed, sequential operation of the concentrator in the manner described below. Controller 40 may also control the timed operation of crossover valve 38. The valves may also be pressure cycle operated. Main valve 28 is programmed to deliver a matched air flow alternately to each of beds 31 and 34. Crossover valve 38 is likewise programmed to deliver a matched or equivalent flow of enriched oxygen between the sieve beds.

Air delivered to beds 31 and 34 is filtered therein to produce enriched oxygen. This oxygen is then directed through oxygen outlet/output lines 42 and 44 and check valves 46 and 48 respectively to product tank 50. From there, the product is directed through a flow meter 52 and delivered to patient 54 as required. Various types of known conduits, tubes, pipes and fittings may be used to communicably connect the sieve beds to tank 50.

The volume of enriched oxygen in tank 50 is monitored by a pressure sensor 51, which is, in turn, connected to motor 18, through DC motor control 21. When sensor 51 detects that the product tank is filled to a selected pressure, motor control 21 causes motor 18 to halt operation. As a result, the battery is not needlessly drained when the product tank is full. The motor operates more efficiently and battery life is prolonged. Alternating types of sensors/controls may be used to selectively stop the motor when the product tank approaches or reaches a full condition.

In operation, motor 18 employs a constant amperage controlled by circuit 20 (as described more fully below). The motor thereby operates compressor 12 to pump air sequentially to sieve beds 31 and 34. In particular, air is drawn through air intake 22 and pressurized by pressure head 14. Pressurized air is directed by arrow 60 into pressure reservoir 26. Controller 40 is programmed so that main valve 28 initially delivers pressurized air from reservoir 26 through communicable connection 32 to sieve bed 31. This air is then filtered by the filtering medium in the sieve bed and delivered through valve 46 to tank 50. At the same time, vacuum head 16 draws a vacuum upon sieve bed 34 through vacuum reservoir 30, main valve 28 and communicable connection 36.

At a predetermined time, controller 40 reverses the connection of sieve beds 31 and 34 to pressure and vacuum reservoirs 26 and 30 respectively. Specifically, main valve 28 communicably joins pressure reservoir 26 to sieve bed 34 through connection 36. At the same time, the main valve communicably joins sieve bed 31 to vacuum reservoir 30 through connection 32. A large volume of pressurized air from reservoir 26 is introduced into bed 34. This air is filtered by the medium in bed 34 and then delivered through line 44 and check valve 48 to enriched oxygen tank 50. Meanwhile, nitrogen and other impurities remaining in sieve bed 31 from the prior cycle are evacuated from sieve bed 31 through main valve 28 and into vacuum reservoir 30. The impurities are then drawn by pressure head 16 and discharged by exhaust port 24. Check valve 46 prevents previously enriched oxygen from being drawn in reverse from tank 50.

The concentrator continues to sequentially cycle in a timed, controlled manner so that enriched oxygen is continuously produced and impurities contemporaneously removed in a cyclical, alternating manner from the respective sieve beds. Shortly before the end of each pressurization cycle, controller 40 opens crossover valve 38 so that the sieve bed being pressurized delivers oxygen through the crossover valve to the bed undergoing evacuation. For example, shortly (i.e. approximately one second) before sieve bed 31 is fully pressurized, crossover valve 38 opens so that some of the oxygen already produced and remaining in sieve bed 31 is directed via valve 33 to sieve bed 34. This oxygen helps to strip or purge nitrogen and other impurities previously filtered by sieve bed 34 during the prior cycle. It is therefore much easier for these impurities to be evacuated to vacuum reservoir 30. An analogous operation occurs toward the end of the pressurization cycle of sieve bed 34. Oxygen is directed through open crossover valve 38 from bed 34 to bed 31 to assist purging of nitrogen and other impurities from the latter bed and thereby enrich the oxygen in that bed.

By directing enriched oxygen through the crossover valve before the main valve reverses the air flow to the beds, system 10 achieves a number of benefits. Prolonged and increased purging is performed in each filter so that improved nitrogen filtration and oxygen enrichment are accomplished. Additionally, pressure is relieved/reduced in the bed being pressurized prior to, rather than following the end of each pressure cycle. This reduces the power used by the compressor so that operating efficiency and battery life are improved. Concentrator 10 therefore represents a significant improvement over less than optimally efficient conventional systems wherein the crossover valve does operate to purge nitrogen and the pressure in the beds is not equalized until after the valves reverse the pressure cycle.

In the foregoing manner, enriched oxygen is continuously produced by sieve beds 31 and 34 in a cyclical, alternating sequence. The oxygen is delivered to tank 50 and received by patient 54 through flow meter 52 as needed. Impurities are evacuated from the beds in a reverse alternating sequence and the check valves restrict reverse flow of oxygen from tank 50. The vacuum and pressure reservoirs significantly reduce the pressure exerted on the beds and the compressor while maintaining a high volume air flow. Efficiency is improved and power requirements are reduced. These benefits are enhanced by utilizing sensors to deactivate the motor when the oxygen tank is full, as previously described.

The valves are programmed or otherwise controlled to provide equal air flow volume during each cycle. This optimizes the level of oxygen provided to the patient. Unlike concentrator sieve beds of the prior art, both beds work at an equal level and produce an equally pure oxygen output. This improves the level of enriched oxygen delivered to tank 50. The system of this invention thus operates much more efficiently than conventional concentrators.

Concentrator 10 uniquely employs pressure and vacuum reservoirs 26 and 30, which provide for significant advantages over the prior art. These benefits are as follows.

1. The aluminum or other metal construction of pressure reservoir 26 causes the reservoir to act as a heat sink. The reservoir effectively dissipates heat from the pressurized air produced by compressor 12. This cools the air eventually delivered to sieve beds 31 and 34. As a result, the sieve beds operate more efficiently and effectively to produce enriched oxygen.

2. Pressure reservoir 26 significantly reduces the volume of water droplets entering the sieve beds. Instead, such water is retained in the pressure reservoir. The water droplets are converted to vapor during periods of low pressure so that the beds operate more effectively and efficiently.

3. The use of pressure reservoir 26 significantly reduces the pressure of the air delivered to the sieve beds. As a result, the concentrator requires less power and the beds filter the air much more efficiently. In fact, when the amperage of the motor is controlled as described more fully below, this allows a greater volume of air to be generated so that improved oxygen enrichment is achieved. By the same token, when less pressure is generated, the motor is far less apt to stall. Because the motor and compressor do not have to work as hard to build high pressure, much less power is required and battery life is significantly prolonged. Extended battery life is especially important for portable concentrators. The expense and inconvenience at having to continuous change batteries is significantly alleviated.

4. The presence of pressurized air in reservoir 26 enables a large volume of air to be introduced into a sieve bed during each cycle when valve 28 opens reservoir 26 to that sieve bed. A large volume of pressurized air is ready to be immediately introduced into the sieve bed so that the production of enriched oxygen is increased significantly. Indeed, a much more effective enriched oxygen production is achieved than is accomplished by simply pumping air from the compressor directly into the sieve bed. Such improved performance also allows much smaller and more easily transportable sieve beds to be utilized. Much less filter medium is needed to produce a desired volume of enriched oxygen.

5. Because crossover valve 38 opens just before the end of each pressurization cycle, the pressure in the concentrator is reduced. Once again, the motor and compressor are required to work less. System efficiency is improved and battery life is extended.

6. The innovative use of the vacuum reservoir especially improves the efficiency and effectiveness of the concentrator. When valve 28 switches the pressure and vacuum reservoir connections to the respective sieve beds, the presence of vacuum reservoir 30 enables the previously pressurized sieve bed (which is now communicably joined to the vacuum reservoir) to evacuate extremely efficiently and effectively. A high flow of air almost immediately strips nitrogen molecules from the filter medium in the previously pressurized sieve bed. Impurities are then removed through vacuum reservoir 28 to vacuum head 16 and exhaust port 24 of compressor 12. A much more effective evacuation of impurities is thereby accomplished than would be achieved without the vacuum reservoir. In addition, vacuum reservoir 30 helps to reduce the total vacuum drawn by compressor 12. This greatly reduces the overall power consumption and further contributes to prolonged compressor and battery life.

By controlling the amperage of motor 18 rather than the speed (RPM) of the motor as is done in the prior art, significant benefits are achieved. In particular, amperage control 20 provides for an efficient and constant power consumption that further contributes to prolonged battery life. Moreover, the amperage control also accomplishes greater air flow and therefore improved production of enriched oxygen on initial start up.

There is shown in FIG. 2 a graph that compares the air volume and directly proportional motor speed (RPM) to the pressure generated by the compressor. In conventional concentrators, the speed of the motor is selected (for example, a representative speed of 2,000 RPM, line 100) and the pressure generated by the compressor gradually builds so that a volume of air 102 is generated.

The concentrator of this invention alternatively utilizes an amperage control circuit 20 that maintains the motor at a predetermined power consumption suited to operate effectively with the pressure and vacuum reservoirs 26 and 30. Initially, as represented by line 104, and before the air is pressurized, the motor operates at a relatively high speed (e.g. 4,000 RPM) and produces a commensurately high degree of air flow. Gradually, as indicated by arrow 104, the pressure increases while the motor speed and air flow decrease. Nonetheless, this is preferable to constant RPM control, dashed arrow 100, wherein the air flow or volume remains the same or decreases slightly as the pressure in the concentrator builds. Indeed, over the period required to achieve maximum desired pressure, the amperage controlled concentrator will generate a significantly greater amount of air flow, as represented by triangular hatched area 106. An increased production of enriched oxygen is thereby achieved. This high flow achieves a significantly improved production of enriched oxygen in the sieve beds.

Using the amperage control of this system is especially effective when the concentrator is employed in high altitude locations. In such cases, the motor speed must typically be higher during initial operation of the concentrator in order to overcome the lower density of the high altitude air. Thereafter, the amperage control circuit 20 allows the motor speed (RPM) to constantly change in order to maintain the desired volume of air flow in the concentrator. An RPM controlled motor is less than satisfactory in such applications because the air flow remains constant. Amperage control, wherein RPM is gradually reduced after start-up of the concentrator, is much preferred and provides for a more efficient operation and improved production of enriched oxygen.

From the foregoing it may be seen that the apparatus of this invention provides for an oxygen concentrator that produces enriched oxygen for medical purposes utilizing vacuum-pressure swing absorption. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

Other embodiments will occur to those skilled in the art and are within the following claims:

What is claimed is:
1. A vacuum-pressure swing absorption oxygen concentrator comprising:
   a battery powered DC motor;
   a compressor operated by said motor;
   a pressure reservoir having an inlet communicably connected to said compressor and a vacuum reservoir having an outlet communicably connected to said compressor such that operation of said compressor delivers pressurized air to said pressure reservoir and draws a vacuum on said vacuum reservoir;
   a pair of nitrogen filters; and
   a control valve for sequentially and alternately interconnecting an outlet of said pressure reservoir to communicate with a selected one of said nitrogen filters while simultaneously connecting an inlet of said vacuum reservoir to communicate with the other said nitrogen filter; whereby pressurized air from said pressure reservoir is delivered sequentially and alternately to respective one of said nitrogen filters for filtering therein while previously filtered impurities are simultaneously discharged from the other said filter through said vacuum reservoir.

2. The apparatus of claim 1 in which said compressor includes a pair of heads for generating air under pressure and a vacuum respectively.

3. The apparatus of claim 1 further including a motor control mechanism for controlling operation of said motor.

4. The apparatus of claim 3 in which said motor controller includes an amperage control for directing said motor to operate at a constant predetermined amperage.

5. The apparatus of claim 1 further including a control mechanism for directing said control valve to alternately and sequentially interconnect each of said nitrogen filters to said pressure and vacuum reservoirs respectively.

6. The apparatus of claim 5 in which said control mechanism directs said control valve to deliver equal flow volumes of air to each of said filters.

7. The apparatus of claim 1 further including a crossover valve interconnected between said nitrogen filters, which crossover valve opens prior to a respective one of said filters being fully pressurized by air from said pressure reservoir such that pressurized enriched oxygen is delivered through said crossover valve to said other nitrogen filter to assist in purging said other filter of previously filtered impurities contained therein.

8. The apparatus of claim 7 further including a controller for determining a selected pressure level at which said crossover valve opens.

9. The apparatus of claim 8 in which said controller directs said crossover valve to deliver equal amounts of pressurized enriched oxygen to each of said filters.

10. The apparatus of claim 1 further including a product tank communicably connected to an outlet of each said filter for receiving filtered air therefrom.

11. The apparatus of claim 10 in which a check valve is disposed between each said filter and said tank to direct the flow of filtered air in one direction from said filters to the tank while restricting the flow of enriched oxygen from said tank to said filters.

12. The apparatus of claim 10 further including a sensor for detecting that pressurized air in said tank has reached a predetermined level.

13. The apparatus of claim 12 in which said motor is programmed to stop operation of said compressor in response to said sensor detecting said predetermined level of air in said tank.

* * * * *